May 28, 1946. M. A. OWEN Plant Pat. 692
GRAPE VINE
Filed July 10, 1945
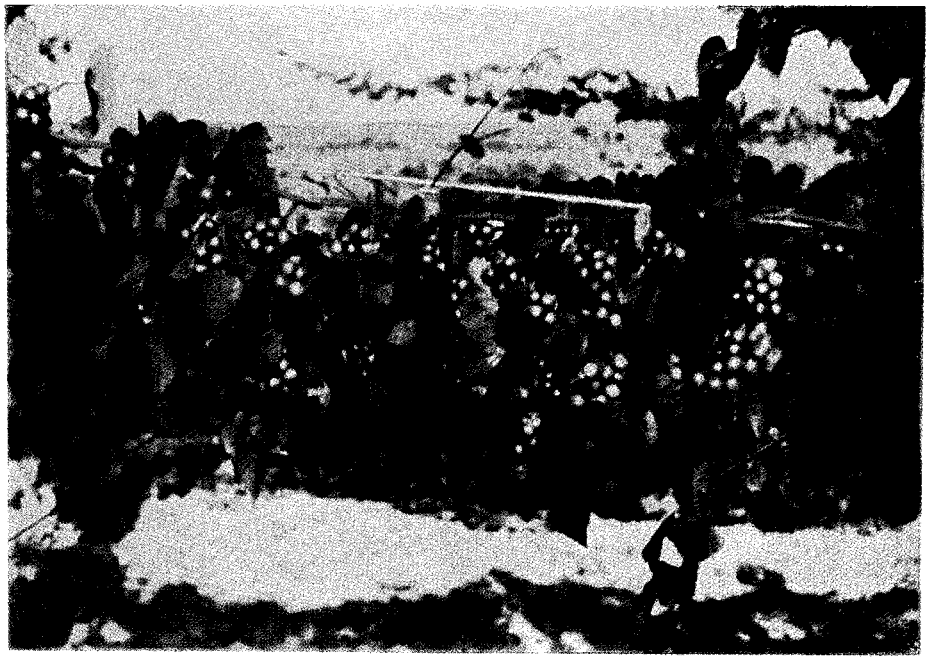
Inventor
M. A. Owen
By Robb & Robb
His attorneys Patented May 28, 1946

Plant Pat. 692

UNITED STATES PATENT OFFICE

692

GRAPEVINE

Marquis Aubrey Owen, Gay, Ga.

Application July 10, 1945, Serial No. 604,120

1 Claim. (Cl. 47—62)

The present discovery relates to a new and distinct variety of grape of the Muscadine class, resembling the ordinary Scuppernong, but differing therefrom in important respects.

The grape herein described was discovered by me as a seedling and brought to my vineyard where, in its development, I found it to possess a number of distinct characteristics as compared with the common Scuppernong, which is one of the leading varieties of the State of Georgia.

More specifically stated, this new variety, when compared with the ordinary Scuppernong, produces bronze berries considerably larger in size and borne in larger clusters as quite well illustrated in the accompanying drawing of a specimen of this variety. The berries also have a considerably higher sugar content.

Further, this new grape is much more prolific, more persistent, more vigorous than the common Scuppernong. As is well known, the latter variety seldom bears two good crops in succession, whereas this new grape bears regularly annually.

I have asexually reproduced this new variety and have found the foregoing characteristics to be established and come true to form.

The following is a detailed description of the new variety, the color terminology referring to the ordinary dictionary definition:

Vine:

*Habit.*—The shoots are more upright in growth than other varieties and the canes are stiff. When in the open with no objects to climb on, it is semi-prostrate, but when near objects or trellises it climbs readily.

*Hardiness.*—The growth is very vigorous and the length of annual growth is from six inches to ten feet, depending upon fertility of soil. The vine has high disease resistance (especially Black Rot).

*Color of bark.*—In new growth the tender shoots are light green with no red color pigment, this coloring gradually changing with age to brownish gray in one season. The older bark is gray.

*Node length.*—⅜ inch average.

*Internode length.*—Average 1½ inches. The first two or three internodes are short, progressively increasing until the average internode length of 1½ inches is reached. Variations of ½ inch to 6 inches have been noted, depending upon fertility of soil.

*Tendrils.*—Average length 4½ inches. The tendrils are light green and may vary in length from 2 to 8 inches, depending upon fertility. Tendrils arise from the fruit cluster.

*Size of stem.*—Average ⅛ to $\frac{3}{16}$ inch caliper on new growth and may increase to ¼ inch in fertile soil.

*Size of trunk.*—A mature or old plant has an average diameter of 3 inches.

Flowers:

*Type.*—The flowers are imperfect. Bearing vines have pistillate type flowers. Flowers are borne in panicle type of inflorescence.

*Normal budding season.*—Ten days to two weeks. Blooming begins in different localities from May 1st to June 15th due to variation in climate.

*Stamens.*—Stamens are not sufficiently developed to be depended upon to produce sufficient pollen for pollinating purposes, though there is some pollen which will, in some cases, enable the plants to set some fruit, but full crops cannot be expected unless a male plant is set separately nearby. Stamens are present in dwarf form varying from 6 to 7 per bloom on the same flower cluster.

Foliage:

*Size.*—Average length from stem base to tip of leaf is 4½ inches. Average width of leaf just above stem base 4 inches.

*Shape.*—Palmate.

*Color.*—The color varies from light green in young foliage to dark green in mature foliage. The veins are lighter in color than the rest of the leaf.

*Texture.*—Smooth; thin; tough; pliable.

*Pubescence.*—Very little on upper side of leaf. Very little on under side of leaf except where veins join.

Fruit:

*Size of cluster.*—1 to 35 berries. The average cluster has 9 berries.

*Compactness.*—Medium.

*Peduncles.*—A peduncle arises opposite the leaf axil. The peduncle has a node about 1 inch from the stem, and at this node a flower cluster and a tendril may arise. On the average, 2 peduncles near the base of the stem develop fruit. The tendril which arises from the peduncle node usually dies after the fruit cluster forms. However, it may develop if an object is close enough for it to grasp. The other peduncles usually develop into strong tendrils to aid the vine in climbing.

*Pedicel.*—The pedicel is $\frac{1}{16}$ to $\frac{1}{12}$ inch in length.

*Brush.*—The brush pulls off in the fruit berry.

*Berry.*—Size: It is round and averages about ¾ inch in diameter. The diameter may range from ⅝ to 1 inch. Color: Light bronze in full sun. Greenish bronze in shade. Shape: Round. Skin: Medium texture. Seed: 3 or 4 per berry.

*Inner flesh.*—Quality—excellent. Color—almost transparent with trace of green. Tenderness — medium. Juiciness — very juicy. Acidity—medium. Sweetness—sugar content above average.

*Ripening period.*—About three weeks. The peak of the ripening season is around September 6th in central Georgia.

*Uses:* Fresh fruit is delightful eating. Juice, processed and refrigerated. Wine. Jam and jellies. Grape seed oil. Cooking.

*Storage quality:* The fruit may be kept three days without refrigeration, and it may be kept indefinitely with refrigeration.

*Propagation:* Layering only.

I claim:

A new and distinct variety of grape vine of the Muscadine class, characterized as to novelty by its large size bronze-colored berries; large size clusters and high sugar content; by its greater prolificacy, more persistent and vigorous growing habit and more regular annual bearing than found in the commonly known Scuppernong, substantially as shown and described.

MARQUIS AUBREY OWEN.